United States Patent [19]

Hofer et al.

[11] 3,951,975

[45] Apr. 20, 1976

[54] O-ALKYL-S-ALKYL-O-[2-SUBSTITUTED-PYRIMIDIN(4)YL]THIONOTHIOLPHOSPHORIC ACID ESTERS

[75] Inventors: Wolfgang Hofer; Fritz Maurer, both of Wuppertal; Ingeborg Hammann, Cologne, all of Germany

[73] Assignee: Bayer Aktiengesellschaft, Leverkusen, Germany

[22] Filed: Dec. 4, 1974

[21] Appl. No.: 529,658

[30] Foreign Application Priority Data

Dec. 6, 1974 Germany............................ 2360877

[52] U.S. Cl........................... 260/251 P; 260/251 R; 424/200
[51] Int. Cl.² ........................ C07D 9/65; A01N 9/36
[58] Field of Search.................................. 260/251 P

[56] References Cited
UNITED STATES PATENTS

| | | | |
|---|---|---|---|
| 2,754,243 | 7/1956 | Gysin et al. ................. | 260/251 P X |
| 3,328,405 | 6/1967 | Simone et al................ | 260/251 P X |

OTHER PUBLICATIONS

Ralls et al., J. Econ. Entomol, 59(5), 1296–1297 (1966).
Thomson et al., Chemical Abstracts, 59, 2832g (1963).

*Primary Examiner*—Richard J. Gallagher
*Assistant Examiner*—Diana G. Rivers
*Attorney, Agent, or Firm*—Burgess, Dinklage & Sprung

[57] ABSTRACT

O-Alkyl-S-alkyl-O-[2-substituted-pyrimidin(4)yl]-thionothiolphosphoric acid esters of the formula

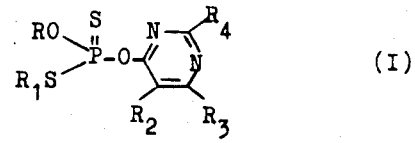

in which
R and $R_1$ are the same or different alkyl radicals each with 1 to 6 carbon atoms,
$R_2$ is hydrogen or alkylmercapto with 1 to 4 carbon atoms,
$R_3$ is hydrogen or methyl, and
$R_4$ is alkyl or alkylmercapto with 1 to 6 carbon atoms, or alkylmercaptoalkylmercapto with 1 to 4 carbon atoms per alkyl moiety, or carbalkoxymethylmercapto with 1 to 4 carbon atoms per alkyl moiety,
which possess insecticidal, acaricidal and nematocidal properties.

7 Claims, No Drawings

O-ALKYL-S-ALKYL-O-[2-SUBSTITUTED-PYRIMIDIN(4)YL]THIONOTHIOLPHOSPHORIC ACID ESTERS

The present invention relates to and has for its objects the provision of particular new 0-alkyl-S-alkyl-O-[2-substituted-pyrimidin(4)yl]-thionothiolphosphoric acid esters optionally further substituted in the 5-position with a lower alkylmercapto radical and/or in the 6-position with a methyl radical, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from German Patent 910,652 that pyrimidin(4)yl-thionophosphoric acid esters, for example O,O-diethyl-O-[2-methyl mercapto-6-methyl-pyrimidin(4)yl]thionophosphoric acid ester (Compound A), exhibit insecticidal and acaricidal properties.

The present invention provides new pyrimidine-thiono-thiolphosphoric acid esters of the general formula

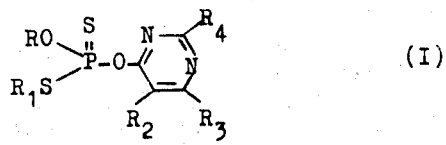

in which
R and R₁ each independently is alkyl with 1 to 6 carbon atoms,
R₂ is hydrogen or lower alkylmercapto,
R₃ is hydrogen or methyl, and
R₄ is alkyl or alkylmercapto with 1 to 6 carbon atoms, or lower alkylmercapto-lower alkyl-mercapto or carbo-lower alkoxymethylmercapto.

Preferably, the lower alkyl radicals of R, R₁, R₂ and/or R₄ have 1 to 4 carbon atoms. More preferably, R and R₁ are straight or branched lower alkyl radicals, especially R being ethyl and R₁ being n-propyl, R₂ is hydrogen, methylmercapto or ethylmercapto, and R₄ is methyl, ethyl, n-propyl, iso-propyl, n-butyl, iso-butyl, tert.-butyl, methylmercapto, ethylmercapto, n-propylmercapto, iso-propylmercapto, methylmercaptomethylmercapto, ethylmercaptoethylmercapto, methylmercaptoethylmercapto, carbomethoxymethylmercapto, carboethoxymethylmercapto or carbo-n-propoxymethylmercapto.

Surprisingly, the pyrimidine-thionothiolphosphoric acid esters (I) according to the invention couple a low toxicity to warm-blooded animals with a substantially higher insecticidal and acaricidal action than the previously known compounds of analogous structure and of the same type of action. Hence, the compounds according to the invention represent a genuine enrichment of the art.

The invention also provides a process for the production of a pyrimidine-thionothiolphosphoric acid ester of formula (I) in which an O,S-dialkylthionothiolphosphoric acid diester halide of the general formula

in which
R and R₁ have the abovementioned meanings and
Hal is halogen, preferably chlorine,
is reacted with a 4-hydroxy-pyrimidine derivative of the general formula

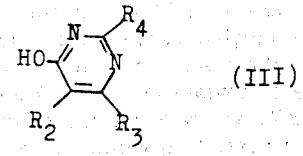

in which
R₂, R₃ and R₄ have the abovementioned meanings, optionally in the form of an alkali metal salt, alkaline earth metal salt or ammonium salt, or in the presence of an acid acceptor.

If, for example, O-ethyl-S-sec.-butyl-thionothiolphosphoric acid diester chloride and 2-ethylmercapto-4-hydroxy-6-methylpyrimidine are used as starting materials, the course of the reaction can be represented by the following formula scheme:

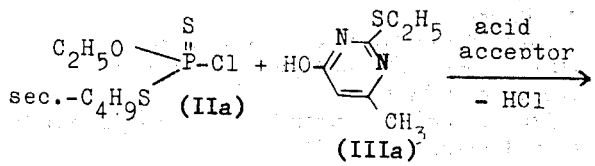

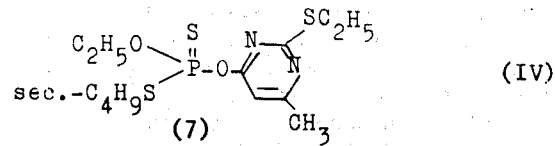

O,S-Dialkylthionothiolphosphoric acid diester halides (II) are described in the literature and can be prepared according to conventional processes, e.g. USSR Patent Specification 184,863 and pulbished Japanese Patent Application 5536/72.

The following are specific examples thereof: O,S-diethyl-, O,S-di-n-propyl-, O,S-di-iso-propyl-, O,S-di-n-butyl-, O,S-di-iso-butyl-, O,S-di-tert.-butyl-, O,S-di-sec.-butyl-, O-ethyl-S-n-propyl-, O-ethyl-S-iso-propyl-, O-ethyl-S-n-butyl-, O-ethyl-S-sec.-butyl-, O-ethyl-S- tert.-butyl-, O-ethyl-S-iso-butyl-, O-n-propyl-S-n-butyl-, O-n-propyl-S-sec.-butyl-, or O-n-butyl-S-n-propyl-thionothiolphosphoric acid ester chloride.

4-Hydroxypyrimidines (III) are described in the literature and can be prepared according to conventional processes.

The following are specific examples thereof: 2-methyl-, 2-ethyl-, 2-n-propyl-, 2-iso-propyl-, 2-n-butyl-, 2-iso-butyl-, 2-sec.-butyl-, 2-tert.-butyl-, 2-methylmercapto-, 2-ethylmercapto-, 2-n-propylmercapto-, 2-isopropylmercapto-, 2-methylthiomethylmercapto-, 2-ethylthioethylmercapto-, 2-methylthioethylmercapto-, 2-carbomethoxymethylmercapto-, 2-carboethoxymethylmercapto- and 2-carbo-n-propoxymethylmercapto-4-hydroxy-6-methylpyrimidine and the compounds which are additionally substituted by methylmercapto or ethylmercapto in the 5-position.

The reaction is preferably carried out in the presence of a solvent which term includes a mere diluent. Practically all inert organic solvents can be used for this purpose. They include, in particular, aliphatic and aromatic optionally chlorinated hydrocarbons, for example, benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate, methylate and ethylate and potassium carbonate, methylate and ethylate, have proved particularly suitable, as have aliphatic, aromatic or heterocyclic amines, for example triethylamine, dimethylaniline, dimethylbenzylamine and pyridine.

The reaction temperature can be varied within a wide range. In general, the reaction is carried out at 0 to 100, preferably at 30° to 60°C.

The reaction is in general allowed to take place under normal pressure.

In carrying out the process, the starting materials are in most cases employed in an equimolar ratio. An excess of one or other reactant seems to produce no significant advantage. In general, the reaction is carried out in a solvent in the presence of an acid acceptor. To complete the reaction, the mixture is in most cases stirred for from one to several hours at elevated temperatures, and cooled, and the reaction mixture is poured into an organic solvent, for example toluene. After washing with saturated sodium bicarbonate solution and water, the organic phase may be dried and the solvent distilled off under reduced pressure. The residue may be generally purified by "slight distillation".

The new compounds are generally obtained in the form of oils which can in most cases not be distilled without decomposition but can be freed from the last volatile constituents by so-called "slight distillation", that is to say by prolonged heating under reduced pressure to moderately elevated temperatures, and can be purified in this way. They are characterized by their refractive indexes.

As has already been mentioned, the pyrimidine-thionothiolphosphoric acid esters (I) according to the invention are distinguished by an outstanding insecticidal and acaricidal action against plant pests, hygiene pests and pests of stored products, coupled with very low toxicity to warm-blooded animals. They possess a good action against sucking and against biting insects and mites (Acarina). Furthermore, some of the compounds also exhibit a soil-insecticidal and/or nematocidal action.

For this reason, the compounds according to the invention are employed successfully in plant protection as well as in the field of hygiene and of the protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips fermoralis*, and bugs, for example the beet bug (*Piesma quadrata*), the red cotton bug (*Dysdercus intermedius*), the bed bug (*Cimex Lectularius*), the assassin bug ((*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Pultella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius = Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for exmaple the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinger fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*) the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usuable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, ect.), alcohols (.e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1% by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50-100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, and more particularly methods of combating insects and acarids, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples.

EXAMPLE 1

Plutella test
Solvent: 3 parts by weight of acetone
Emuslifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the capterpillars were killed whereas 0% means that none of the caterpillars were killed.

The active compounds, the concentrations of the active compounds, the evaluation times and the results can be seen in Table 1:

Table 1

| Active compound | (Plutella test) Active compound concentration in % by weight | Degree of destruction in % after 3 days |
|---|---|---|
| 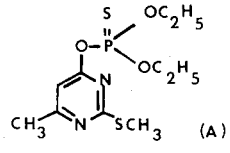 (known) | 0.1<br>0.01 | 100<br>0 |
| 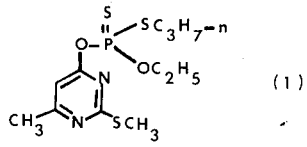 | 0.1<br>0.01 | 100<br>100 |
| 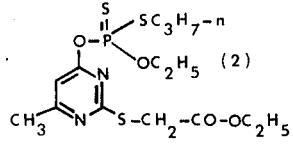 | 0.1<br>0.01 | 100<br>100 |
| 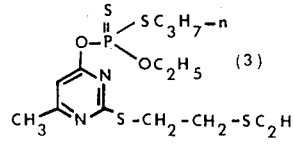 | 0.1<br>0.01 | 100<br>100 |

Table 1-continued

| Active compound | (Plutella test) Active compound concentration in % by weight | Degree of destruction in % after 3 days |
| --- | --- | --- |
| ![structure (4)] | 0.1<br>0.01<br>0.001 | 100<br>100<br>90 |
| ![structure (5)] | 0.1<br>0.01 | 100<br>100 |
| ![structure (6)] | 0.1<br>0.01 | 100<br>100 |

EXAMPLE 2

Tetranychus test (resistant)
Solvent: 3 parts by weight of acetone
Emulsifier: 1 part by weight of alkylaryl polyglycol ether.

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10 – 30 cm, were sprayed with the preparation of the active compound until dripping wet. These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained is expressed as a percentage: 100% means that all the spider mites were killed whereas 0% means that none of the spider mites were killed.

The active compounds, the concentrations of the active compounds, the evaluation times and the results can be seen in Table 2.

Table 2

| Active compound | (Tetranychus test/resistant) Active compound concentration in % by weight | Degree of destruction in % after 2 days |
| --- | --- | --- |
| 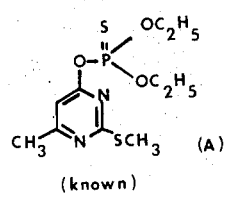<br>(known) | 0.1 | 0 |

Table 2-continued (Tetranychus test/resistant)

| Active compound | Active compound concentration in % by weight | Degree of destruction in % after 2 days |
|---|---|---|
| (1) [structure: 2-methylthio-4-methyl-pyrimidin-6-yl O-ethyl S-n-propyl phosphorothiolothionate] | 0.1<br>0.01<br>0.001 | 100<br>100<br>60 |
| (3) [structure: 2-(ethylthioethylthio)-4-methyl-pyrimidin-6-yl O-ethyl S-n-propyl phosphorothiolothionate] | 0.1<br>0.01 | 100<br>90 |
| (4) [structure: 2-isopropyl-4-methyl-pyrimidin-6-yl O-ethyl S-n-propyl phosphorothiolothionate] | 0.1 | 98 |
| (5) [structure: 2-isopropylthio-4-methyl-pyrimidin-6-yl O-ethyl S-n-propyl phosphorothiolothionate] | 0.1<br>0.01 | 100<br>99 |
| (6) [structure: 2-isopropyl-4-methyl-5-methylthio-pyrimidin-6-yl O-ethyl S-n-propyl phosphorothiolothionate] | 0.1 | 99 |

The following example illustrates the preparation of the 4-hydroxy-pyrimidine derivatives (III) used as starting materials for the process of the invention.

EXAMPLE 3

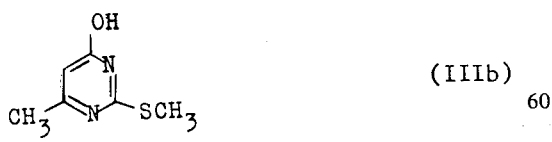

(IIIb)

A solution of 120 g of sodium hydroxide (3 moles) in 250 ml of water was added dropwise at room temperature to a mixture of 195 g (1.5 moles) of acetoacetic acid ethyl ester, 210 g (0.76 mole) of S-methylisothiourea sulfate and 300 ml of water and the batch was allowed to react for a further 18 hours at room temperature. The reaction mixture was then acidified with acetic acid and the product which had crystallized out was filtered off and rinsed thoroughly with water. 224 g (96% of theory) of 2-methylmercapto-4-hydroxy-6-methyl-pyrimidine were obtained in the form of a colorless powder of melting point 219°C.

The following compounds were prepared analogously:

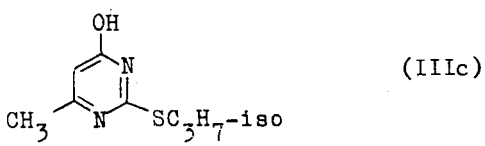

(IIIc)

of melting point 149°C, yield 75% of theory.

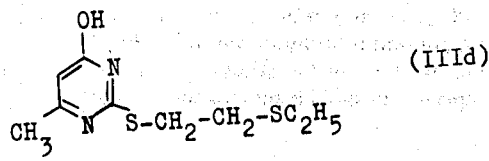

(IIId)

of melting point 94°C, yield 91% of theory.

b.

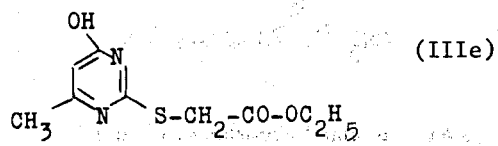

(IIIe)

175 g (1.05 moles) of bromoacetic acid ethyl ester were added dropwise at 50°–60°C to a suspension of 142 g (1 mole) of 4-methyl-2-thiouracil and 71.5 g. (1.05 moles) of sodium ethylate in 1 liter of ethanol. The reaction mixture was allowed to complete reacting for 2½ hours at 70°–80°C and was then poured into 2 liters of water. The product which had crystallized out was filtered off and well rinsed with ether. 173 g (76% of theory) of 2-carboethoxy-methylmercapto-4-hydroxy-6-methylpyrimidine was obtained in the form of a beige powder of melting point 139°C.

c.

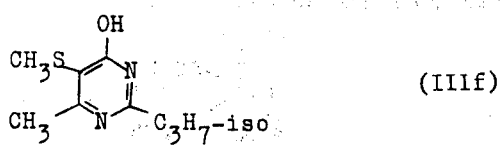

(IIIf)

A mixture of 19 g (0.15 mole) of isobutyramidine hydrochloride, 35 ml of methanol, 8.1 g (0.15 mole) of sodium methylate and 27 g (0.15 mole) of 2-methylmercaptoacetoacetic acid ethyl ester was stirred for 4 hours at 60°–70°C. The solvent was then distilled off under reduced pressure, the residue was dissolved in warm water and the solution was neutralized with acetic acid. The product which had crystallized out was filtered off. 13 g (44% of theory) of 2-isopropyl-4-hydroxy-5-methylmercapto-6-methylpyrimidine were obtained in the form of a colorless powder of melting point 156°C.

The following compound was obtained analogously:

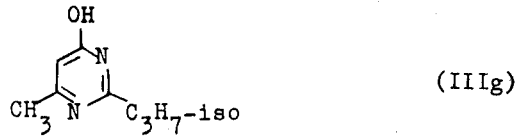

(IIIg)

of melting point 173°C, yield 66% of theory.

Intermediates so prepared are used to prepare the novel end products as shown in the following example.

EXAMPLE 4

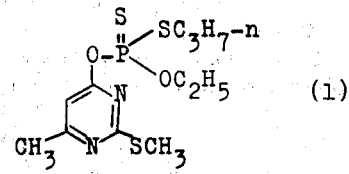

(1)

21.8 g (0.1 mole) of O-ethyl-S-n-propyl-thionothiolphosphoric acid ester chloride were added dropwise to a mixture of 15.6 g (0.1 mole) of 2-methylmercapto-4-hydroxy-6-methyl-pyrimidine, 20.7 g (0.15 mole) of potassium carbonate and 300 ml of acetonitrile and the batch was allowed to react for a further 3 hours at 45°–50°C. The reaction mixture was then cooled, poured into 500 ml of toluene and washed with saturated sodium bicarbonate solution and with water. The organic phase was then dried over sodium sulfate and freed from the solvent under reduced pressure, and the residue was subjected to "slight distillation". 28 g (83% of theory) of O-ethyl-S-n-propyl-O-[2-methylmercapto-6-methyl-pyrimidin(4)yl]-thionothiolphosphoric acid ester were obtained in the form of a yellow oil of refractive index $n_D^{21}$ : 1.5694.

The following compounds of the formula

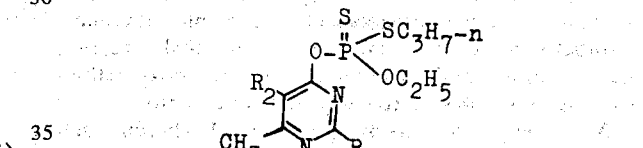

were obtained analogously to Example 1.

| Compound No. | R₄ | R₂ | Yield (% of theory) | Refractive index | |
|---|---|---|---|---|---|
| 2 | —S—CH₂—CO—OC₂H₅ | H | 85 | $n_D^{23}$: | 1.5520 |
| 3 | —S—CH₂—CH₂—SC₂H₅ | H | 80 | $n_D^{23}$: | 1.5719 |
| 4 | —C₃H₇—iso | H | 81 | $n_D^{21}$: | 1.5208 |
| 5 | —S—C₃H₇—iso | H | 87 | $n_D^{23}$: | 1.5606 |
| 6 | —C₃H₇—iso | SCH₃ | 48 | $n_D^{23}$: | 1.5403 |

Other compounds which can be similarly prepared include:

O,S-dimethyl-O-[2-(4'-methylthio-butylmercapto)-5-butylmercapto-pyrimidin(4)yl]-thionothiol phosphoric acid ester, O-sec.-butyl-S-ethyl-O-[2-(2'-methyl-2'-butyl-thioethylmercapto)-5-isopropylmercapto-6-methylpyrimidin(4)yl]-thionothiolphosphoric acid ester, O-isopropyl-S-n-butyl-O-[2-methyl-5-ethylmercapto-6-methylpyrimidin(4)yl]-thionothiol phosphoric acid ester, O-ethyl-S-n-propyl-O-[2-n-butyl-6-methyl-pyrimidin(4)yl]-thionothiol phosphoric acid ester, O-ethyl-S-n-propyl-O-[2-n-butylmercapto-6-methyl-pyrimidin(4)yl]-thionothiol phosphoric acid ester, O-ethyl-S-n-propyl-O-[2-propoxycarbonylmethylmercapto-6-methyl-pyrimidin(4)yl]-thionothiol phosphoric acid ester, and the like.

What is claimed is:

1. An O-alkyl-S-alkyl-O-pyrimidin(4)yl-thionothiolphosphoric acid ester of the formula

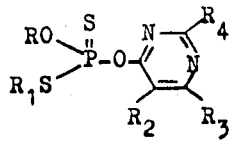 (I)

in which
R and $R_1$ each independently is alkyl with 1 to 6 carbon atoms,
$R_2$ is hydrogen or lower alkylmercapto,
$R_3$ is hydrogen or methyl, and
$R_4$ is alkylmercapto with 1 to 6 carbon atoms, or lower alkylmercapto-lower alkylmercapto, or carbo-lower alkoxymethylmercapto, the lower alkyl and alkoxy moieties having 1 to 4 carbon atoms.

2. A compound according to claim 1 in which R and $R_1$ each independently is a straight or branched alkyl radical with 1 to 4 carbon atoms, $R_2$ is hydrogen, methylmercapto or ethylmercapto, and $R_4$ is methylmercapto, ethylmercapto, n-propylmercapto, iso-propylmercapto, methylmercaptomethylmercapto, ethylmercaptoethylmercapto, methylmercaptoethylmercapto, carbomethoxymethylmercapto, carboethoxymethylmercapto or carbo-n-propoxymethylmercapto.

3. A compound according to claim 1 wherein such compound is O-ethyl-S-n-propyl-O-[2-methylmercapto-6-methyl-pyrimidin(4)yl]-thionothiolphosphoric acid ester of the formula

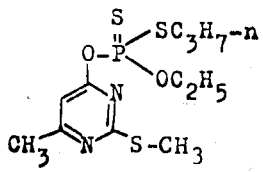

4. A compound according to claim 1 wherein such compound is O-ethyl-S-n-propyl-O-[2-ethoxycarbonylmethylmercapto-6-methyl-pyrimidin(4)yl]-thionothiolphosphoric acid ester of the formula

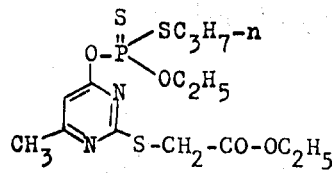

5. A compound according to claim 1 wherein such compound is O-ethyl-S-n-propyl-O-[2-(2'-ethylthio-ethylmercapto)-6-methyl-pyrimidin(4)yl]-thionothiolphosphoric acid ester of the formula

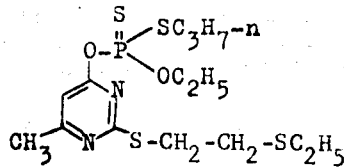

6. A compound according to claim 1 wherein such compound is **O-ethyl-S-n-propyl-O-[2-isopropylmercapto-6-methyl-pyrimidin(4)yl]-thionothiolphosphoric acid ester of the formula

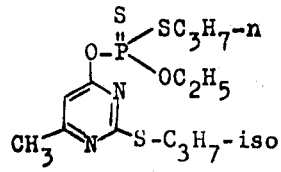

7. A compound according to claim 1, in which R is ethyl and $R_1$ is n-propyl.

* * * * *